United States Patent [19]
Åsum

[11] Patent Number: 5,836,810
[45] Date of Patent: Nov. 17, 1998

[54] ABRADING OR POLISHING DEVICE

[76] Inventor: Thomas Åsum, Fridkullagatan 26, Göteborg, Sweden

[21] Appl. No.: 364,491

[22] Filed: Dec. 27, 1994

[30] Foreign Application Priority Data

Jan. 4, 1994 [SE] Sweden ................................ 9400017

[51] Int. Cl.⁶ ........................... B24D 15/04; A61C 15/00
[52] U.S. Cl. ........................ 451/526; 433/142; 433/166
[58] Field of Search ..................... 451/523, 524, 451/526, 525, 557; 433/142, 166; 76/81.1, 81.4, 81.5, 81.6, 81

[56] References Cited

U.S. PATENT DOCUMENTS

| | | | |
|---|---|---|---|
| 501,127 | 7/1893 | Wofford | 451/490 |
| 1,479,030 | 1/1924 | Dobbins | 76/81.6 |
| 1,926,171 | 9/1933 | Owens | 76/81.1 |
| 2,862,298 | 12/1958 | Weigele | 32/58 |
| 3,091,061 | 5/1963 | Bahr | 51/170 |
| 3,624,908 | 12/1971 | Ricketts et al. | 32/58 |
| 4,030,198 | 6/1977 | Gerber | 32/58 |
| 4,592,729 | 6/1986 | Bilciurescu | 433/142 |

FOREIGN PATENT DOCUMENTS

| | | |
|---|---|---|
| 1046828 | 7/1959 | Germany . |
| WO90/14050 | 11/1990 | WIPO . |

*Primary Examiner*—Robert A. Rose
*Attorney, Agent, or Firm*—Foley & Lardner

[57] ABSTRACT

A device for abrading or polishing primarily uneven objects, comprising an abrasive section in the form of a strip which is preferably essentially in-elastic and which is coated with an abrasive or polishing layer. One end of the ribbon shows an elastic section connected to the abrasive section. Such a device allows a reciprocating movement without moving the end of the ribbon which is inserted into the mouth of the patient.

21 Claims, 3 Drawing Sheets

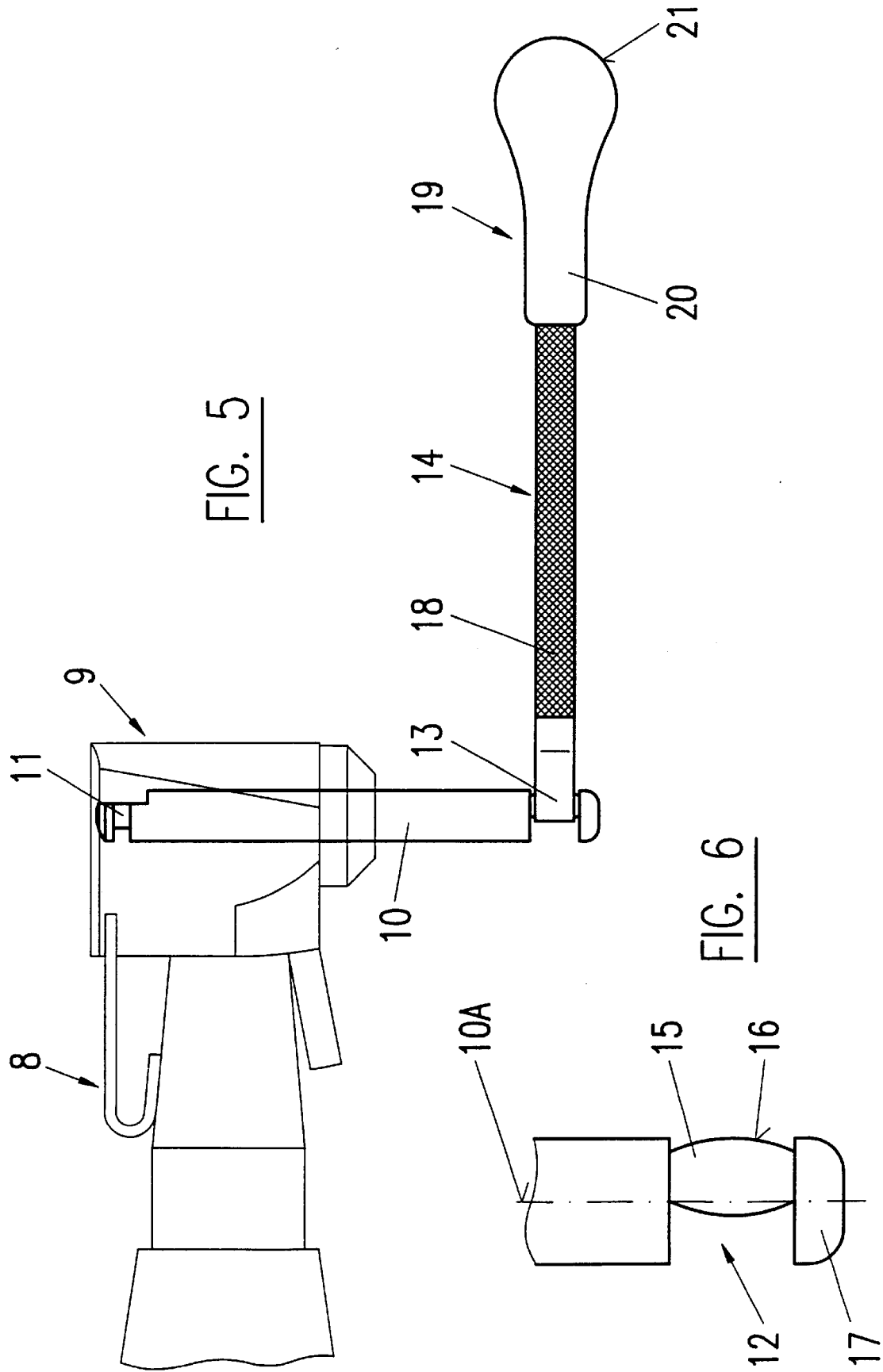

ABRADING OR POLISHING DEVICE

BACKGROUND OF THE INVENTION

This invention concerns a device for abrading or polishing mainly uneven objects such as teeth, where access can be restricted, consisting of an abrasive section in the form of a strip, which is primarily essentially inelastic and which is coated with an abrasive or polishing layer.

In dentistry, approximal treatment of teeth often occurs, such as finishing and polishing fillings etc. Since the gap between teeth is frequently small, small strips with abrasive or polishing elements have been developed to get between the teeth and polish fillings. These ribbons or "strips" are hand-held and require that both ends of the strip are held and moved back and forth to prevent the strip from bending when it is inserted between the teeth, and to achieve sufficient pressure and reciprocating movement in relation to the tooth to be polished.

This means that in general one of the dentist's hands must be inside the patient's mouth to be able to grip the inner end of the strip and provide the reciprocating movement, which causes inconvenience to both the patient and the dentist. Because use of the strip is uncomfortable, material removal is slow and difficult, which further increases the inconvenience.

Because of these problems, various methods and devices have been developed in the light of known technology to make things easier for both patient and dentist. Various more or less suitable devices have been developed to hold the strip, where the majority have the strip tensioned between two attachments, and some kind of handle, such as U.S. Pat. No. 4,592,729 for example, so that the device can be operated with one hand outside the mouth.

The known devices are either manual or motor-driven to achieve the reciprocating movement of the strip. They have however been found to be relatively clumsy or unsuitable in other ways and have not become wide spread.

Another known device is the so-called Profin system, where an angled attachment is mounted on a dentist's drill and is provided with diamond-coated tips, which are given a reciprocating movement, when they are inserted between the teeth to grind or polish fillings approximally. This in general functions in a satisfactory manner, but requires relatively expensive investment in equipment and can be difficult to use on the rear teeth, when the device must be located inside or outside the tooth to be polished.

The ribbons or "strips" are usually of the disposable type and are thrown away after use, whereas the holder devices and Profin system have to be cleaned and sterilized after use, which causes further cost and considerable expenditure of time.

Despite the previously mentioned attempts to solve the problems, no simple, cost-effective method for polishing teeth which is less inconvenient to the patient has been developed.

SUMMARY OF THE INVENTION

Based on this prior art, an object of the present invention is to provide for a generally useful, efficient and cost-effective device which is simple in use and causes the minimum of inconvenience to the patient, in polishing teeth. This object is attained with a device wherein one of its end is provided with an elastic section, which is connected to the abrasive section

BRIEF DESCRIPTION OF THE DRAWINGS

The invention is explained in more detail hereinafter with reference to a drawing of embodiments.

FIG. 5 shows in a side view and in a partial section a third embodiment of the invention used in a dentist apparatus, FIG. 6 shows a detail of a spindle for the apparatus of FIG. 5 adapted for the use of an abrasive ribbon.

DETAILED DESCRIPTION OF THE INVENTION

Figure 1:
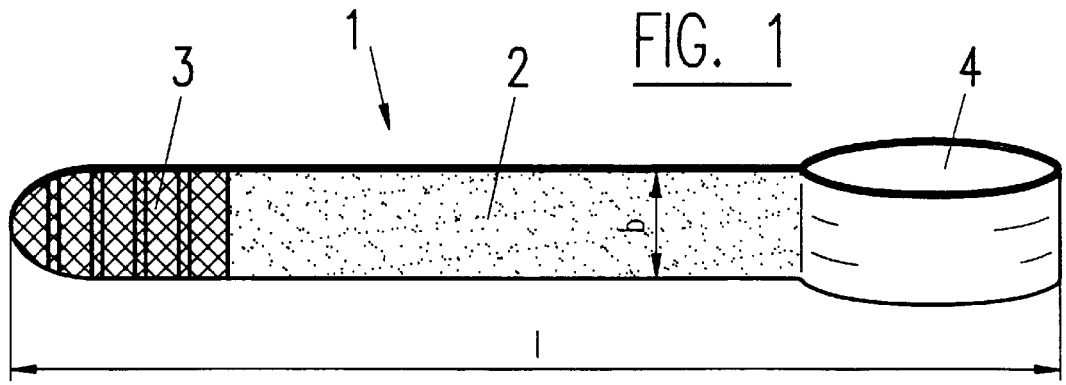
FIG. 1 shows a side view of the abrasive ribbon or abrasive "strip" in the position of use in its first preferred embodiment.
Figure 2:
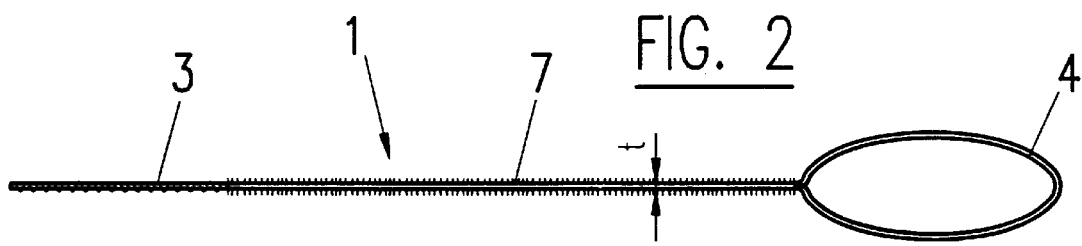
FIG. 2 shows a view from above of the abrasive strip of FIG. 1.

The first embodiment of the abrading or polishing device according to FIG. 1 comprises an abrasive ribbon or abrasive strip 1, which in the first embodiment in accordance with FIGS. 1 and 2 comprises an abrasive section 2 made of a suitable non-elastic material, such as impregnated card, plastic or stainless steel for example, with a width b of 2–4 mm for example, which is coated in known manner with an abrasive or polishing layer 7. The ribbon or strip section 2 is preferably somewhat flexible, to conform itself to suit the contours of the object to be sanded. The thickness t is small, as is shown in FIG. 2, for example one or several tenths of a millimeter, to facilitate location of the strip between two adjacent teeth.

The inner section, i.e. the part which is in the patient's mouth, consists of an elastic section 3, made from a suitable elastic material, such as rubber or plastic for example, and is especially structured to make it easier for the dentist's fingers when that person holds the elastic section 3. The elastic section 3 is joined to the abrasive section 2 in a suitable manner, to form a unit.

The outer section, i.e. the section which is outside the patient's mouth, is equipped with a non-elastic holding means 4. The holding means can be a loop, for example, for one finger of the dentist's other hand, or for an eccentrically mounted spindle on a dentist's drill or hand piece, or consists of a structured, non-elastic ribbon section or a handle of other design. The entire device has a length 1 of about 50 mm, for example.

Figure 3:
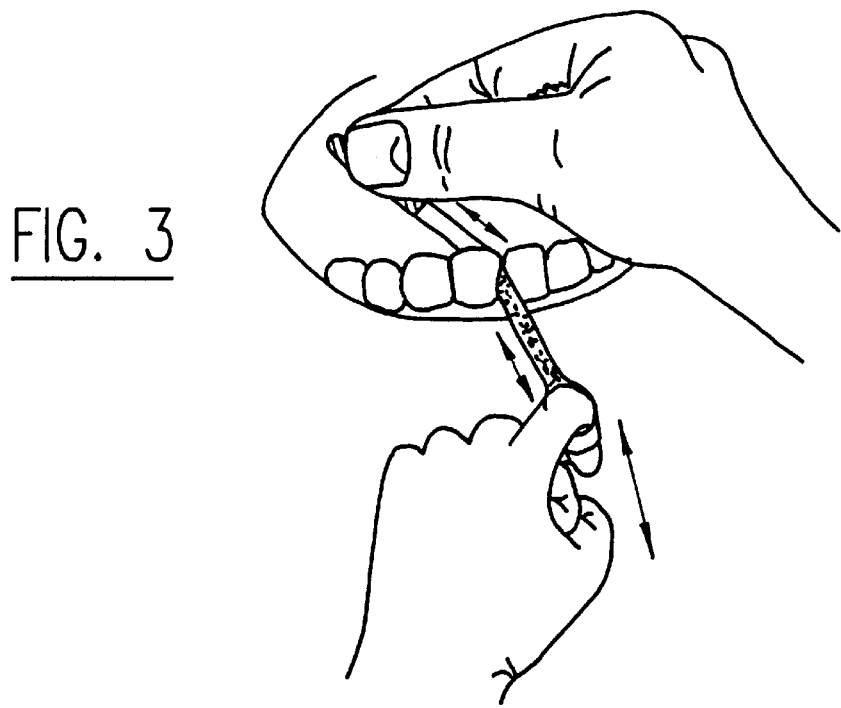
FIG. 3 shows the use of the strip of FIG. 1 for treating teeth approximally.

FIG. 3 shows how the abrasive ribbon 1 or abrasive strip can be used for treating such things as a tooth filling approximally. The strip 1 is inserted between the teeth and the inner elastic section 3 is held tight by the fingers of one hand.

The other hand grasps the outer holding means 4, and by alternately pulling and releasing the hand holding the holding means 4, at the same time as the other hand is kept still in the mouth cavity, a reciprocating movement is obtained thanks to the elastic section held by the first hand. This gives much faster and simpler removal of material or polishing compared with the conventional abrading strip which must be moved back and forth with both hands, and considerably less discomfort to the patient.

The abrasive strip can either be of the disposable type, and is then preferably made from plastic or impregnated card for cost reasons, or of the multiple use type, and is then preferably made from stainless steel so that it can be cleaned and sterilized by autoclaving, for example, or by means of an ultrasound bath.

Compared with the mechanical devices, such as the Profin system for example, the device according to the present invention is much more advantageous as regards cost and is more supple and simpler to operate.

Within the scope of the invention, other dimensions, choice of material, configurations and applications are possible. For example, the strip can be used for abrading and polishing other objects, especially uneven ones. The elastic section 3 can be of another type and can be composed of a metal tension spring, and does not need to be hand held, it can be fastened to a holder. The holding means 4 can have various configurations to be connected to the reciprocating driving means to achieve the reciprocating motion. The main point is however that one of the ends of the strip is elastic or is provided with an elastic element, e.g. a tension spring, to achieve the desired reciprocating motion of the abrasive element, although the outer part of the previously mentioned end is stationary in relation to the object to be abraded.

Figure 4:
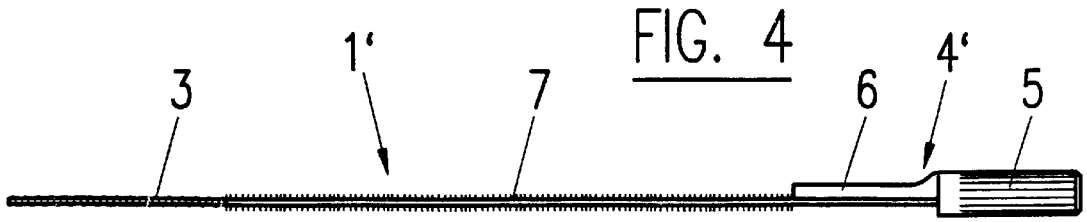
FIG. 4 shows a view from above of a second preferred embodiment of the abrasive strip of the invention.

FIG. 4 shows an example of another embodiment of the holding means, which has been designated 4', whereas the rest of the device, designated 1' is unchanged. In this embodiment, holding means 4' is a cylindrical or tapered pin 5 which narrows slightly towards the outside, which is attached by welding, bonding etc. to strip 2 via a narrower joining piece 6. A suitable material for pin 5 and joining piece 6 is plastic. Pin 5 is furthermore dimensioned so that it can be fastened in a tool which gives the strip its reciprocating movement. For example, pin 5 can be adapted to suit the Profin system mentioned in the introduction.

From that which has been said above, it is clear that the invention must not be limited to the preferred embodiments, as described above and shown on the drawings, but it can also be subject to modifications within the scope of that which is stated in the claims below.

FIGS. 5 and 6 disclose the use of an abrasive ribbon with a dental handpiece. This apparatus is known and not part of the invention. Hand piece 8 has a head 9 for receiving a spindle 10, whereby the connecting part 11 of the spindle is standard. The receiving end 12 of the spindle is formed to receive the non-elastic connection end 13 of the ribbon 14. The connection end 12 comprises a receiving piece 15 having a smaller diameter than the spindle and being disposed eccentrically in regard to the axis 10 A of spindle 10. Receiving piece 15 has a convex surface 16 and ends into a cup-like endpiece 17 which secures firmly the loop of the ribbon. The surface of the receiving piece may also be concave.

Ribbon 14 comprises loop 13 at one end, the abrasive strip part 18 which does not extend to the loop and the elastic hand holding portion 19. This holding portion 19 in FIG. 5 consists of an elastic section 20 and a holding means 21.

Figure 7:
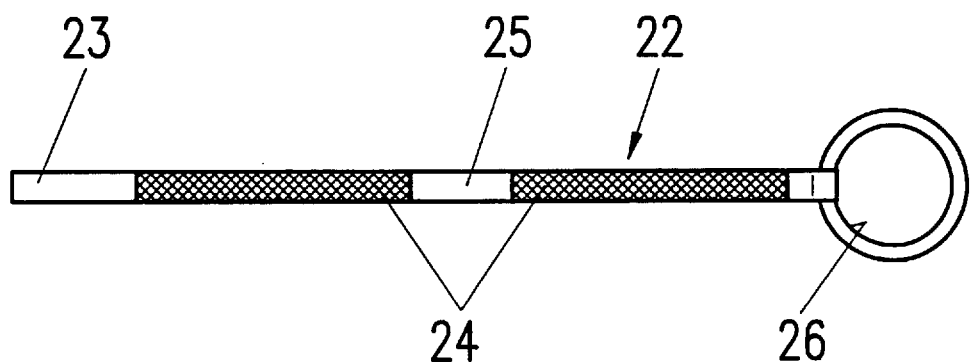
FIG. 7 shows a variant of the abrasive ribbon of FIG. 5 in a side view.
Figure 8:
FIG. 8 shows the abrasive ribbon of FIG. 6 in a view from above.

In the embodiment of FIGS. 7 and 8 ribbon 22 is composed of loop 23 for receiving the spindle, abrasive strip part 24 with one window 25 without abrasive layer for insertion between the teeth, followed by an O-ring 26 or the like elastic ring as elastic holding means. This construction of the ribbon allows a relatively cheap and simple production. It is possible to preview two different grinding particle sizes for the two abrasive strip parts with window.

Both ribbons 14 and 22 are produced by welding and assembling together the different parts, similar to the production of ribbon 1.

I claim:
1. A device which may be resiliently extended in use for abrading tooth surfaces, said device comprising:
    an abrasive section in the form of a strip, which is substantially inelastic in a longitudinal direction, and which is coated with an abrasive layer; and
    an elastic section connected to the abrasive section at one end and which may be held stationary at the other end thereof.
2. A device according to claim 1, wherein the elastic section has a structured surface.
3. A device for abrading mainly uneven objects, comprising an abrasive section in the form of a strip, which is substantially inelastic in a longitudinal direction of the strip, and which is coated with an abrasive layer, wherein a first end of the device is provided with an elastic section which is connected to a first end of the abrasive section, wherein the elastic section is made of a material selected from the group consisting of rubber and elastomer.
4. A device according to claim 1, wherein the elastic section is an elastic O-ring, connected to the ribbon and serving as holding means.
5. A device according to claim 1, wherein a holding means is connected to a second end of the abrasive section.
6. A device which may be resiliently extended in use for abrading mainly uneven objects said device comprising:
    an abrasive section in the form of a strip, which is substantially inelastic in a longitudinal direction and which is coated with an abrasive layer; and
    an elastic section connected to the abrasive section at one end and which may be held stationary at the other end thereof,
    wherein a holding means is connected to the other end of the abrasive section and, wherein the holding means includes a loop.
7. A device which may be resiliently extended in use for abrading mainly uneven objects, said device comprising:
    an abrasive section in the form of a strip, which is substantially inelastic in a longitudinal direction, and which is coated with an abrasive layer; and
    an elastic section connected to the abrasive section at one end and which may be held stationary at the other end thereof,
    wherein a holding means is connected to the other end of the abrasive section and, wherein the holding means includes a cylindrical pin.
8. A device according to claim 1, wherein the abrasive section consists of a non-elastic material.
9. A device which may be resiliently extended in use for abrading mainly uneven objects said device comprising:
    an abrasive section in the form of a strip, which is substantially inelastic in a longitudinal direction, and which is coated with an abrasive layer; and
    an elastic section connected to the abrasive section at one end and which may be held stationary at the other end thereof,
    wherein the abrasive section consists of a non-elastic material and, wherein the abrasive section comprises a window without abrasive layer.
10. A device which may be resiliently extended in use for abrading mainly uneven objects, said device comprising:
    an abrasive section in the form of a strip, which is substantially inelastic in a longitudinal direction, and which is coated with an abrasive layer; and
    an elastic section connected to the abrasive section at one end and which may be held stationary at the other end thereof, wherein the material in a substrate of the abrasive section is selected from the group consisting of plastic, metal and card.

11. A device for abrading mainly uneven objects, comprising an abrasive section in the form of a strip, which is substantially inelastic in a longitudinal direction of the strip, and which is coated with an abrasive layer, wherein a first end of the device is provided with an elastic section which is connected to a first end of the abrasive section, wherein the device comprises at a second end a loop for receiving a spindle and at the first end the elastic means comprising a holding means.

12. The device of claim 11 in combination with a dentist apparatus, the dentist apparatus including the spindle having a receiving end with a receiving piece having a central axis which is eccentric in regard to a central axis of the spindle and has a smaller diameter than the spindle, wherein the second end of the device engages the receiving end of the spindle.

13. The device according to claim 12, wherein a surface of the receiving piece of the spindle is concave.

14. A device which may be resiliently extended in use for abrading mainly uneven objects, said device comprising:
   an abrasive section in the form of a strip, which is substantially inelastic in a longitudinal direction, and which is coated with an abrasive layer; and
   an elastic section connected to the abrasive section at one end and which may be held stationary at the other end thereof, wherein the elastic section is made of rubber.

15. A device which may be resiliently extended in use for abrading mainly uneven objects, said device comprising:
   an abrasive section in the form of a strip, which is substantially inelastic in a longitudinal direction, and which is coated with an abrasive layer; and
   an elastic section connected to the abrasive section at one end and which may be held stationary at the other end thereof, wherein the elastic section is made of elastomer.

16. A device according to claim 1, wherein the elastic section comprises a tension spring.

17. A device according to claim 5, wherein the holding means includes a tapered pin.

18. A device for abrading tooth surfaces, comprising an abrasive section in the form of a strip, which is substantially inelastic in a longitudinal direction of the strip, and which is coated with an abrasive layer, wherein a first end of the device is provided with an elastic section which is connected to a first end of the abrasive section, wherein the elastic section comprises a tension spring.

19. A device which may be resiliently extended in use for polishing tooth surfaces, said device comprising:
   a polishing section in the form of a strip, which is substantially inelastic in a longitudinal direction, and which is coated with a polishing layer,
   an elastic section connected to the polishing section at one end and which may be held stationary at the other end thereof.

20. A device which may be resiliently extended in use for polishing mainly uneven objects, said device comprising:
   a polishing section in the form of a strip, which is substantially inelastic in a longitudinal direction, and which is coated with a polishing layer; and
   an elastic section connected to the polishing section at one end and which may be held stationary at the other end thereof, wherein the elastic section is made of a material selected from the group consisting of rubber and elastomer.

21. A device according to claim 19, wherein the elastic section comprises a tension spring.

* * * * *